United States Patent [19]

Edwards et al.

[11] Patent Number: 5,457,125
[45] Date of Patent: Oct. 10, 1995

[54] OXIME DERIVATIVES

[75] Inventors: Philip N. Edwards, Bramhall; Michael S. Large, Stoke-on-Trent, both of England

[73] Assignees: Zeneca Limited, London, England; Zeneca Pharma S.A., Cergy Cedex, France

[21] Appl. No.: 293,181

[22] Filed: Aug. 19, 1994

Related U.S. Application Data

[62] Division of Ser. No. 59,275, May 11, 1993, Pat. No. 5,376,680.

[30] Foreign Application Priority Data

May 12, 1992 [EP]  European Pat. Off. ............. 92401291

[51] Int. Cl.⁶ ..................... A61K 31/35; A61K 31/34; C07D 309/10; C07D 307/04
[52] U.S. Cl. ............... 514/459; 549/60; 549/414; 549/415; 549/472; 548/214; 548/213; 548/198; 548/193; 548/189; 548/186; 546/256; 546/268; 546/283; 546/284; 544/336; 544/357; 514/471; 514/444; 514/372; 514/359; 514/269; 514/365; 514/340; 514/336; 514/255
[58] Field of Search ..................... 549/415, 414, 549/472, 60; 548/214, 213, 198, 193, 189, 186; 546/256, 268, 283, 284; 544/357, 336; 514/459, 471, 444, 372, 365, 340, 336, 359, 269, 255

[56] References Cited

U.S. PATENT DOCUMENTS

| | | |
|---|---|---|
| 4,567,184 | 1/1986 | Musser et al. . |
| 4,625,034 | 11/1986 | Neiss et al. . |
| 4,631,287 | 12/1986 | Chakraborty et al. . |
| 4,661,596 | 4/1987 | Kreft, III et al. . |
| 4,681,940 | 7/1987 | Musser et al. . |
| 4,725,619 | 2/1988 | Chakraborty et al. . |
| 4,728,668 | 3/1988 | Chakraborty et al. . |
| 4,794,188 | 12/1988 | Musser et al. . |
| 4,839,369 | 6/1989 | Youssefyeh et al. . |
| 4,868,193 | 9/1989 | Lee . |
| 4,874,769 | 10/1989 | Youssefyeh et al. . |
| 4,876,346 | 10/1989 | Musser et al. . |
| 5,006,534 | 4/1991 | Mohrs et al. . |
| 5,098,930 | 3/1992 | Edwards et al. . |
| 5,098,932 | 3/1992 | Hamon . |
| 5,105,020 | 4/1992 | Girodeau . |
| 5,134,148 | 7/1992 | Crawley et al. . |
| 5,137,913 | 8/1992 | Bird et al. . |
| 5,179,115 | 1/1993 | Bruneau et al. . |
| 5,196,419 | 3/1993 | Crawley . |
| 5,208,259 | 5/1993 | Bird et al. . |
| 5,214,070 | 5/1993 | Bird et al. . |
| 5,217,969 | 6/1993 | Bruneau et al. . |
| 5,217,977 | 6/1993 | Crawley et al. . |
| 5,217,978 | 6/1993 | Bird . |
| 5,219,881 | 6/1993 | Hamon . |
| 5,221,677 | 6/1993 | Crawley et al. . |
| 5,225,438 | 7/1993 | Dowell et al. . |
| 5,234,950 | 8/1993 | Edwards et al. . |
| 5,236,919 | 8/1993 | Crawley et al. . |
| 5,236,948 | 8/1993 | Waterson . |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0462820 | 12/1991 | European Pat. Off. . |

*Primary Examiner*—Nicky Chan
*Attorney, Agent, or Firm*—Cushman Darby & Cushman

[57] ABSTRACT

The invention concerns oxime derivatives of the formula I

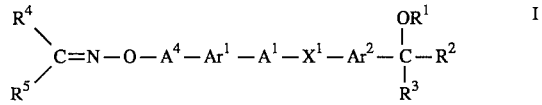

wherein $R^4$ is hydrogen, (1–4C)alkyl, halogeno-(2–4C)alkyl, hydroxy-(2–4C)alkyl, cyano-(1–4C)alkyl, phenyl or phenyl-(1–4C)alkyl;

$R^5$ is hydrogen, (1–4C)alkyl, halogeno-(2–4C)alkyl, hydroxy-(2–4C)alkyl, cyano-(1–4C)alkyl, phenyl or phenyl-(1–4C)alkyl, or a heteroaryl moiety selected from pyridyl, pyrimidinyl, pyrazinyl, pyridazinyl, furyl, thienyl, oxazolyl and thiazolyl;

$A^4$ is (1–4C)alkylene;

$Ar^1$ is phenylene, pyridinediyl or pyrimidinediyl;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl or thiazolediyl;

$R^1$ is hydrogen, (1–4C)alkyl, (3–4C)alkenyl or (3–4C)alkynyl; and $R^2$ and $R^3$ together form a group of the formula $-A^2-X^2-A^3-$ wherein each of $A^2$ and $A^3$ is independently (1–3C)alkylene and $X^2$ is oxy, thio, sulphinyl, sulphonyl or imino;

or a pharmaceutically-acceptable salt thereof;

processes for their manufacture; pharmaceutical compositions containing them and their use as 5-lipoxygenase inhibitors.

6 Claims, No Drawings

OXIME DERIVATIVES

This is a division of application Ser. No. 08/059,275, filed May 11, 1993, now U.S. Pat. No. 5,376,680.

This invention concerns oxime derivatives and more particularly oxime derivatives which are inhibitors of the enzyme 5-lipoxygenase (hereinafter referred to as 5-LO). The invention also concerns processes for the manufacture of said oxime derivatives and novel pharmaceutical compositions containing them. Also included in the invention is the use of said oxime derivatives in the treatment of various inflammatory and/or allergic diseases in which the direct or indirect products of 5-LO catalysed oxidation of arachidonic acid are involved, and the production of new medicaments for such use.

As stated above the oxime derivatives described hereinafter are inhibitors of 5-LO which enzyme is known to be involved in catalysing the oxidation of arachidonic acid to give rise via a cascade process to the physiologically active leukotrienes such as leukotriene $B_4$ ($LTB_4$) and the peptidolipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application Nos. 0375404 A2 and 0385662 A2 that certain heterocyclic derivatives possess inhibitory properties against 5-LO. Furthermore European Patent Applications Nos. 0409413 and 0420511 are also concerned with heterocyclic derivatives which possess inhibitory properties against 5-LO. We have now discovered that certain oxime derivatives which possess some structural features which are similar to those of the compounds disclosed in the above-mentioned applications but which possess other structural features, in particular oxime groups, which were not envisaged in those earlier applications are effective inhibitors of the enzyme 5-LO and thus of leukotriene biosyntheses. Thus such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided an oxime derivative of the formula I

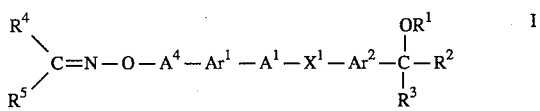

wherein $R^4$ is hydrogen, (1–4C)alkyl, halogeno-(2–4C)alkyl, hydroxy-(2–4C)alkyl, cyano-(1–4C)alkyl, phenyl or phenyl-(1–4C)alkyl; $R^5$ is hydrogen, (1–4C)alkyl, halogeno-(2–4C)alkyl, hydroxy-(2–4C)alkyl, cyano-(1–4C)alkyl, phenyl or phenyl-(1–4C)alkyl, or a heteroaryl moiety selected from pyridyl, pyrimidinyl, pyrazinyl, pyridazinyl, furyl, thienyl, oxazolyl and thiazolyl;

or $R^4$ and $R^5$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy;

$A^4$ is (1–4C)alkylene which may optionally bear one or two substituents selected from (1–4C)alkyl, phenyl and phenyl-(1–4C)alkyl;

wherein each phenyl or phenyl-(1–4C)alkyl group, or each heteroaryl moiety in $R^4$, $R^5$ or $A^4$ may optionally bear one or two substituents selected from halogeno, cyano, trifluoromethyl, hydroxy, amino, nitro, (1–4C)alkyl, (1–4C)alkoxy, (1–4C)alkylamino, di-(1–4C)alkylamino, (1–4C)alkylthio, (1–4C)alkylsulphinyl and (1–4C)alkylsulphonyl;

$Ar^1$ is phenylene, pyridinediyl or pyrimidinediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl or thiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is hydrogen, (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy;

or wherein $R^1$ and $R^2$ together form a group of the formula —$A^2$—$X^2$—$A^3$— which together with the oxygen atom to which $A^2$ is attached and with the carbon atom to which $A^3$ is attached define a ring having 5 or 6 ring atoms wherein $A^2$ and $A^3$, which may be the same or different, each is (1–3C)alkylene and $X^2$ is oxy, thio, sulphinyl or sulphonyl and which ring may bear one, two or three (1–4C)alkyl substituents, and wherein $R^3$ is (1–4C)alkyl, (2–4C)alkenyl or (2–4C)alkynyl; or a pharmaceutically-acceptable salt thereof.

According to a further feature of the invention there is provided an oxime derivative of the formula I wherein $R^4$ is hydrogen, (1–4C)alkyl, halogeno-(2–4C)alkyl, hydroxy-(2–4C)alkyl, cyano-(1–4C)alkyl, phenyl or phenyl-(1–4C)alkyl;

$R^5$ is hydrogen, (1–4C)alkyl, halogeno-(2–4C)alkyl, hydroxy-(2–4C)alkyl, cyano-(1–4C)alkyl, phenyl or phenyl-(1–4C)alkyl;

or $R^4$ and $R^5$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy;

$A^4$ is (1–4C)alkylene which may optionally bear one or two substituents selected from (1–4C)alkyl, phenyl and phenyl-(1–4C)alkyl;

wherein each phenyl or phenyl-(1–4C)alkyl group in $R^4$, $R^5$ or $A^4$ may optionally bear one or two substituents selected from halogeno, cyano, trifluoromethyl, hydroxy, amino, (1–4C)alkyl, (1–4C)alkoxy, (1–4C)alkylamino, di-(1–4C)alkylamino, (1–4C)alkylthio, (1–4C)alkylsulphinyl and (1–4C)alkylsulphonyl;

$Ar^1$ is phenylene, pyridinediyl or pyrimidinediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl or thiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein each of $A^2$ and $A^3$ is independently (1–3C)alkylene and $X^2$ is oxy, thio, sulphinyl, sulphonyl or imino, and which ring may optionally bear one or two substituents selected from hydroxy, (1–4C)alkyl and (1–4C)alkoxy; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as it is well known that oxime derivatives may exist in different geometric isomeric forms, commonly designated as (E)- or (Z)-isomers, the invention includes in its definition any such geometric isomeric form which possesses the property of inhibiting 5-LO. The separation of such geometric isomeric forms may be possible by the standard laboratory techniques of organic chemistry such as by chromatographic separation of a mixture of said isomeric forms or by crystallisation of one such isomeric form from a mixture thereof.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form.

Suitable values for the generic terms referred to above include those set out below.

A suitable value for $R^4$ or $R^5$ when it is (1–4C)alkyl is, for example, methyl, ethyl, propyl, isopropyl or butyl; when it is halogeno-(2–4C)alkyl is, for example, 2-fluoroethyl, 2-chloroethyl, 2-bromoethyl, 3-fluoropropyl or 3-chloropropyl; when it is hydroxy-(2–4C)alkyl is, for example, 2-hydroxyethyl or 3-hydroxypropyl; when it is cyano-(1–4C)alkyl is, for example, cyanomethyl, 1-cyanoethyl, 2-cyanoethyl, 2-cyanoprop-2-yl or 3-cyanopropyl; and when it is phenyl-(1–4C)alkyl is, for example, benzyl, phenethyl or 3-phenylpropyl.

A suitable value for $R^5$ when it is a heteroaryl moiety selected from pyridyl, pyrimidinyl, pyrazinyl, pyridazinyl, furyl, thienyl, oxazolyl and thiazolyl is, for example 2-, 3- or 4-pyridyl, 2-, 4- or 5-pyrimidinyl, 2-pyrazinyl, 3- or 4-pyridazinyl, 2- or 3-furyl, 2- or 3-thienyl, 2-, 4- or 5-oxazolyl or 2-, 4- or 5-thiazolyl.

A suitable value for $A^4$ when it is (1–4C)alkylene is, for example, methylene, ethylene or trimethylene. Suitable values for the substituents which may be present on $A^4$ include, for example:

for (1–4C)alkyl: methyl, ethyl, propyl, isopropyl and butyl;

for phenyl-(1–4C)alkyl: benzyl and phenethyl.

When two such substituents are present they may be located on any of the carbon atoms in said (1–4C)alkylene group, including, for example, both substituents on the same carbon atom.

Suitable values for substituents which may be present when $R^4$ or $R^5$ is phenyl or phenyl-(1–4C)alkyl or a heteroaryl moiety, when $A^4$ bears a phenyl or phenyl-(1–4C)alkyl substituent, or for substituents on $Ar^1$ or $Ar^2$, include, for example:

for halogeno: fluoro, chloro and bromo;

for (1–4C)alkyl: methyl, ethyl, propyl and isopropyl;

for (1–4C)alkoxy: methoxy, ethoxy, propoxy and isopropoxy;

for (1–4C)alkylamino: methylamino, ethylamino and propylamino;

for di-(1–4C)alkylamino: dimethylamino, diethylamino and N-ethyl-N-methylamino;

for (1–4C)alkylthio: methylthio, ethylthio and propylthio;

for (1–4C)alkylsulphinyl: methylsulphinyl, ethylsulphinyl and propylsulphinyl;

for (1–4C)alkylsulphonyl: methylsulphonyl, ethylsulphonyl and propylsulphonyl.

A suitable value for $Ar^1$ or $Ar^2$ when it is phenylene is, for example, 1,3- or 1,4-phenylene.

A suitable value for $A^1$ when it is (1–4C)alkylene is, for example, methylene, ethylene or trimethylene.

A suitable value for $Ar^1$ or $Ar^2$ when it is pyridinediyl, pyrimidinediyl, thiophenediyl, furandiyl or thiazolediyl is, for example, 2,4-, 2,5- or 3,5-pyridinediyl, 4,6-pyrimidinediyl, 2,4- or 2,5-thiophenediyl, 2,4- or 2,5-furandiyl or 2,4- or 2,5-thiazolediyl.

A suitable value for $R^1$ when it is (1–4C)alkyl is, for example, methyl, ethyl, propyl or butyl; when it (3–4C)alkenyl is, for example allyl, 2-butenyl or 3-butenyl; and when it is (3–4C)alkynyl is, for example, 2-propynyl or 2-butynyl.

When $R^2$ and $R^3$ together, when $R^4$ and $R^5$ together, or when $R^1$ and $R^2$ together form a group of the formula $—A^2—X^2—A^3—$ then a suitable value for $A^2$ or $A^3$, which may be the same or different when each is (1–3C)alkylene is, for example, methylene, ethylene or trimethylene. Suitable values for the substituents which may be present on the ring so formed include, for example:

(1–4C)alkyl: methyl, ethyl, propyl, isopropyl, butyl and isobutyl;

for (1–4C)alkoxy: methoxy, ethoxy, propoxy, isopropoxy and butoxy.

Said substituents may be located on any available position including, when the substituent is (1–4C)alkyl, on the nitrogen atom when $X^2$ is imino.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, oxime derivatives of the formula I, or pharmaceutically-acceptable salts thereof, wherein:

(a) $R^4$ is hydrogen, (1–4C)alkyl, phenyl or phenyl-(1–4C)alkyl and wherein said phenyl or phenyl-(1–4C)alkyl group may optionally bear one or two substituents selected from halogeno, (1–4C)alkyl and (1–4C)alkoxy; and $R^5$, $A^4$, $Ar^1$, $A^1$, $X^1$, $Ar^2$, $R^1$, $R^2$ and $R^3$ have any of the meanings defined hereinbefore or in this section defining particular compounds;

(b) $R^5$ is hydrogen, (1–4C)alkyl, halogeno-(2–4C)alkyl, cyano-(1–4C)alkyl, phenyl or phenyl-(1–4C)alkyl and wherein said phenyl or phenyl-(1–4C)alkyl group may optionally bear one or two substituents selected from halogeno, (1–4C)alkyl and (1–4C)alkoxy; and $R^4$, $A^4$, $Ar^1$, $A^1$, $X^1$, $Ar^2$, $R^1$, $R^2$ and $R^3$ have any of the meanings defined hereinbefore or in this section defining particular compounds;

(c) $R^5$ is a heteroaryl moiety selected from pyridyl, pyrimidinyl, furyl, thienyl and thiazolyl which may optionally bear one or two substituents selected from halogeno, nitro, (1–4C)alkyl and (1–4C)alkoxy; and $R^4$, $A^4$, $Ar^1$, $A^1$, $X^1$, $Ar^2$, $R^1$, $R^2$ and $R^3$ have any of the meanings defined hereinbefore or in this section defining particular compounds;

(d) $A^4$ is methylene or ethylene which may optionally bear one or two substituents selected from methyl, ethyl, phenyl and benzyl; and $R^4$, $R^5$, $Ar^1$, $A^1$, $X^1$, $Ar^2$, $R^1$, $R^2$ and $R^3$ have any of the meanings defined hereinbefore or in this section defining particular compounds;

(e) $A^4$ is methylene which may optionally bear one or two substituents selected from methyl and ethyl; and $R^4$, $R^5$, $Ar^1$, $A^1$, $X^1$, $Ar^2$, $R^1$, $R^2$ and $R^3$ have any of the meanings defined hereinbefore or in this section defining particular compounds;

(f) $Ar^1$ is phenylene which may optionally bear one or two substituents selected from halogeno, (1–4C)alkyl and (1–4C)alkoxy; and $R^4$, $R^5$, $A^4$, $A^1$, $X^2$, $Ar^1$, $R^1$, $R^2$ and $R^3$ have any of the meanings defined hereinbefore or in this section defining particular compounds;

(g) $Ar^1$ is 2,4-, 2 5- or 3 5-pyridinediyl; and $R^4$, $R^5$, $A^4$, $A^1$, $X^1$, $Ar^2$, $R^1$, $R^2$ and $R^3$ have any of the meanings defined hereinbefore or in this section defining particular compounds;

(h) $Ar^1$ is 2,5-pyridinediyl (with the $—A^1—X^1—$ group in the 2-position); and $R^4$, $R^5$, $A^4$, $A^1$, $X^1$, $Ar^2$, $R^1$, $R^2$ and $R^3$ have any of the meanings defined hereinbefore or in this section defining particular compounds;

(i) $A^1$ is a direct link to $X^1$; $R^4$, $R^5$, $A^4$, $Ar^1$, $Ar^2$, $X^1$, $R^1$, $R^2$ and $R^3$ have any of the meanings defined hereinbefore or in this section defining particular compounds;

(j) $A^1$ is (1–4C)alkylene and $X^1$ is oxy; and $R^4$, $R^5$, $A^4$, $Ar^1$, $Ar^2$, $R^1$, $R^2$ and $R^3$ have any of the meanings defined hereinbefore or in this section defining particular compounds;

(k) $A^1$ is a direct link to $X^1$ and $X^1$ is thio; and $R^4$, $R^5$, $A^4$, $Ar^1$, $Ar^2$, $R^1$, $R^2$ and $R^3$ have any of the meanings defined hereinbefore or in this section defining particular compounds;

(l) $Ar^2$ is phenylene which may optionally bear one or two substituents selected from halogeno, trifluoromethyl, amino, (1–4C)alkyl and (1–4C)alkoxy, or $Ar^2$ is pyridinediyl, pyrimidinediyl or thiophenediyl; and $R^4$, $R^5$, $A^4$, $Ar^1$, $A^1$, $X^1$, $R^1$, $R^2$ and $R^3$ have any of the meanings defined hereinbefore or in this section defining particular compounds;

(m) $Ar^2$ is thiophenediyl or thiazolediyl; and $R^4$, $R^5$, $A^4$, $Ar^1$, $A^1$, $X^1$, $R^1$, $R^2$ and $R^3$ have any of the meanings defined hereinbefore or in this section defining particular compounds;

(n) $R^1$ is (1–4C)alkyl; and $R^4$ $R^5$ $A^4$ $Ar^1$ $A^1$ $X^1$ $Ar^2$ $R^2$ and $R^3$ have any of the meanings defined hereinbefore or in this section defining particular compounds;

(o) $R^2$ and $R^3$ together form a group of the formula $—A^2—X^2—A^3—$ which together with the carbon atom to which $A^2$ and $A^3$ are attached define a ring having 5 or 6 ring atoms, wherein each of $A^2$ and $A^3$ is independently (1–3C)alkylene and $X^2$ is oxy, and which ring may optionally bear one or two (1–4C)alkyl substituents; and $R^4$, $R^5$, $A^4$, $Ar^1$, $A^1$, $X^1$, $Ar^2$ and $R^1$ have any of the meanings defined hereinbefore or in this section defining particular compounds; and (p) $R^1$ and $R^2$ together form a group of the formula $-A^2-X^2-A^3-$ which together with the oxygen atom to which $A^2$ is attached and with the carbon atom to which $A^3$ is attached define a ring having 5 ring atoms, wherein each of $A^2$ and $A^3$ is methylene and $X^2$ is oxy, and which ring may optionally bear one or two substituents selected from methyl and ethyl, and $R^3$ is methyl or ethyl; and $R^4$, $R^5$, $A^4$, $Ar^1$, $A^1$, $X^1$ and $Ar^2$ have any of the meanings defined hereinbefore or in this section defining particular compounds.

A preferred compound of the invention comprises an oxime derivative of the formula I wherein $R^4$ is hydrogen, methyl, ethyl, propyl, phenyl or benzyl, and wherein said phenyl or benzyl group may optionally bear one or two substituents selected from fluoro, chloro, methyl and methoxy;

$R^5$ is hydrogen, methyl, ethyl, propyl, phenyl or benzyl, and wherein said phenyl or benzyl group may optionally bear one or two substituents selected from fluoro, chloro, methyl and methoxy;

$A^4$ is methylene which may optionally bear one or two substituents selected from methyl, ethyl, phenyl and benzyl, and wherein said phenyl or benzyl group may optionally bear one or two substituents selected from fluoro, chloro, methyl and methoxy;

$Ar^1$ is 1,4-phenylene which may optionally bear one substituent selected from fluoro, chloro, methyl and methoxy;

$A^1$ is a direct link to $X^1$ and $X^1$ is thio or is methylene and $X^1$ is oxy;

$Ar^2$ is 1,3- or 1,4-phenylene which may optionally bear one or two substituents selected from fluoro, chloro, trifluoromethyl, amino, methyl and methoxy, or $Ar^2$ is 3,5-pyridinediyl, 4,6-pyrimidinediyl, 2,4-thiophenediyl or 2,5-thiophenediyl;

$R^1$ is methyl, ethyl or allyl; and $R^2$ and $R^3$ together form a group of the formula $-A^2-X^2-A^3-$ which together with the carbon atom to which $A^2$ and $A^3$ are attached define a ring having 6 ring atoms, wherein each of $A^2$ and $A^3$ is ethylene and $X^2$ is oxy, and which ring may optionally bear one or two substituents selected from methyl and ethyl;

or a pharmaceutically-acceptable salt thereof.

A further preferred compound of the invention comprises an oxime derivative of the formula I wherein $R^4$ is hydrogen, methyl, ethyl, propyl, phenyl or benzyl, and wherein said phenyl or benzyl group may optionally bear one or two substituents selected from fluoro, chloro, methyl and methoxy;

$R^5$ is hydrogen, methyl, ethyl, propyl, phenyl, benzyl, pyridyl, pyrimidinyl, furyl, thienyl or thiazolyl, and wherein said 7 last mentioned groups may optionally bear one or two substituents selected from fluoro, chloro, nitro, methyl and methoxy; or $R^4$ and $R^5$ together form a group of the formula $-A^2-X^2-A^3$ wherein $A^2$ is methylene or ethylene, $A^3$ is ethylene and $X^2$ is oxy;

$A^4$ is methylene which may optionally bear one or two substituents selected from methyl, ethyl, phenyl and benzyl, and wherein said phenyl or benzyl group may optionally bear one or two substituents selected from fluoro, chloro, methyl and methoxy;

$Ar^1$ is 1,4-phenylene which may optionally bear one substituent selected from fluoro, chloro, methyl and methoxy, or $Ar^1$ is 2,5-pyridinediyl (with the $A^1$ group in the 2-position);

$A^1$ is a direct link to $X^1$ and $X^1$ is thio, or $A^1$ is methylene and $X^1$ is oxy;

$Ar^2$ is 1,3- or 1,4-phenylene which may optionally bear one or two substituents selected from fluoro, chloro, trifluoromethyl, amino, methyl and methoxy, or $Ar^2$ is 3,5-pyridinediyl, 4,6-pyrimidinediyl, 2,4-thiophenediyl, 2,5-thiophenediyl, 2,4-thiazolediyl or 2,5-thiazolediyl;

$R^1$ is hydrogen, methyl, ethyl or allyl; and $R^2$ and $R^3$ together form a group of the formula $-A^2-X^2-A^3$ which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or a pharmaceutically-acceptable salt thereof.

A further preferred compound of the invention comprises an oxime derivative of the formula I wherein $R^4$ is hydrogen, methyl, ethyl, phenyl or benzyl; $R^5$ is hydrogen, methyl, ethyl, phenyl or benzyl; $A^4$ is methylene which may optionally bear one or two substituents selected from methyl, ethyl, phenyl and benzyl;

wherein each phenyl or benzyl group in $R^4$, $R^5$ or $A^4$ may optionally bear one or two substituents selected from fluoro, chloro, methyl and methoxy;

$Ar^1$ is 1,4-phenylene;

$A^1$ is a direct link to $X^1$;

$X^1$ is thio;

$Ar^2$ is 1,3-phenylene which may optionally bear one or two substituents selected from fluoro and chloro, or $Ar^2$ is 2,4- or 2,5-thiophenediyl;

$R^1$ is methyl, ethyl or allyl; and $R^2$ and $R^3$ together form a group of the formula $-A^2-X^2-A^3-$ which together with the carbon atom to which $A^2$ and $A^3$ are attached define a ring having 6 ring atoms, wherein each of $A^2$ and $A^3$ is ethylene and $X^2$ is oxy, and which ring may optionally bear one or two methyl substituents;

or a pharmaceutically-acceptable salt thereof.

A further preferred compound of the invention comprises an oxime derivative of the formula I wherein $R^4$ is hydrogen, methyl or phenyl;

$R^5$ is methyl, phenyl, 2-pyridyl or 5-nitro-2-furyl;

or $R^4$ and $R^5$ together form a group of the formula $-A^2-X^2-A^3-$ wherein each of $A^2$ and $A^3$ is ethylene and $X^2$ is oxy;

$A^4$ is methylene which may optionally bear a methyl substituent;

$Ar^1$ is 1,4-phenylene or 2-chloro-1,4-phenylene (with the $A^1$ group in the 4-position);

$A^1$ is a direct link to $X^1$ and $X^1$ is thio, or $A^1$ is methylene and $X^1$ is oxy;

$Ar^2$ is 1,3-phenylene or 5-fluoro-1,3-phenylene;

$R^1$ is methyl; and $R^2$ and $R^3$ together form a group of the formula $-A^2-X^2-A^3-$ which together with the carbon atom to which $A^2$ and $A^3$ are attached define a ring having 6 ring atoms, wherein each of $A^2$ and $A^3$ is ethylene and $X^2$ is oxy, and which ring may optionally bear a methyl substituent alpha to $X^2$;

or a pharmaceutically-acceptable salt thereof.

A further preferred compound of the invention comprises an oxime derivative of the formula I wherein $R^4$ is methyl or phenyl;

$R^5$ is methyl or phenyl;

$A^4$ is methylene which may optionally bear a methyl substituent;

$Ar^1$ is 1,4-phenylene;

$A^1$ is a direct link to $X^1$;

$X^1$ is thio;

$Ar^2$ is 1,3-phenylene or 5-fluoro-1,3-phenylene;

$R^1$ is methyl; and $R^2$ and $R^3$ together form a group of the formula $—A^2—X^2—A^3—$ which together with the carbon atom to which $A^2$ and $A^3$ are attached define a ring having 6 ring atoms, wherein each of $A^2$ and $A^3$ is ethylene and $X^2$ is oxy, and which ring may optionally bear a methyl substituent alpha to $X^2$;

or a pharmaceutically-acceptable salt thereof.

A specific especially preferred compound of the invention is, for example, the following oxime derivative of the formula I, or a pharmaceutically-acceptable salt thereof:

acetone O-{4-[5-fluoro-3-(4-methoxytetrahydropyran-4-yl)phenylthio]-benzyl}oxime or acetone O-{4-[5-fluoro-3-(4-methoxytetrahydropyran-4-yl)phenylthio]-α-methylbenzyl}oxime.

A further specific especially preferred compound of the invention is, for example, the following oxime derivative of the formula I, or a pharmaceutically-acceptable salt thereof:

5-nitrofuran-2-carboxaldehyde O-{4-[5-fluoro-3-(4-methoxytetrahydropyran-4-yl)phenylthio]benzyl}oxime or acetone O-{2-chloro-4-[5-fluoro-3-(4-methoxytetrahydropyran-4-yl)phenylthio]benzyl}oxime.

A compound of the invention comprising an oxime derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $R^4$, $R^5$, $A^4$, $Ar^1$, $A^1$, $X^1$, $Ar^2$, $R^1$, $R^2$ and $R^3$ have any of the meanings defined hereinbefore, provided that when there is an amino, imino, alkylamino or hydroxy group in $R^4$, $R^5$, $A^4$, $Ar^1$, $Ar^2$, $R^1$, $R^2$ and $R^3$ then any such group may optionally be protected by a conventional protecting group which may be removed when so desired by conventional means.

(a) The reaction, conveniently in the presence of a suitable base, of a compound of the formula II

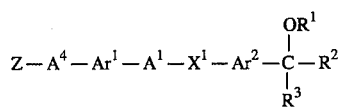

wherein Z is a displaceable group, with an oxime of the formula III

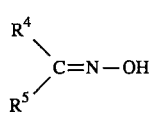

A suitable displaceable group Z is, for example, a halogeno or sulphonyloxy group, for example a chloro, bromo, iodo, methanesulphonyloxy or toluene-4-sulphonyloxy group.

A suitable base for the reaction is, for example, an alkali or alkaline earth metal carbonate, (1–4C)alkoxide, hydroxide of hydride, for example sodium carbonate, potassium carbonate, sodium ethoxide, potassium butoxide, sodium hydroxide, potassium hydroxide, sodium hydride or potassium hydride. The reaction is conveniently performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

The starting materials of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist. The disclosures of European Patent Applications Nos. 0375404, 0385662, 0409413 and 0420511 are particularly relevant to the preparation of suitable starting materials.

(b) The reaction, conveniently in the presence of a suitable base or of a suitable acid, of a compound of the formula IV

with a hydroxylamine of the formula V

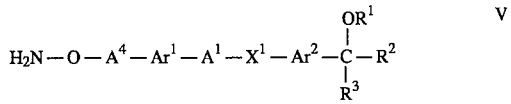

A suitable base for the reaction is, for example, an alkali or alkaline earth metal carbonate, (1–4C)alkoxide, (1–4C)alkanoate, hydroxide or hydride, for example sodium carbonate, potassium carbonate, barium carbonate, sodium ethoxide, potassium butoxide, sodium acetate, sodium hydroxide, potassium hydroxide, sodium hydride or potassium hydride. Alternatively a suitable base for the reaction is, for example, an organic amine base such as pyridine, 2,6-lutidine, collidine, 4-dimethylaminopyridine, triethylamine, N-methylmorpholine or diazabicyclo[5.4.0]undec-7-ene.

A suitable acid for the reaction is, for example, an inorganic acid such as hydrochloric, sulphuric or phosphoric acid, or, for example, an organic acid such as glacial acetic acid, 4-toluenesulphonic acid or trifluoroacetic acid.

The reaction is conveniently performed in a suitable inert solvent or diluent, for example, one or more of water, a (1–4C)alcohol such as methanol, ethanol and propanol, pyridine, 1,2-dimethoxyethane, tetrahydrofuran or a dipolar aprotic solvent such as N,N-dimethylformamide and dimethylsulphoxide. The reaction is conveniently performed at a temperature in the range, for example, 10° to 150° C. conveniently at or near 70° C.

The starting materials of the formula V may be obtained by standard procedures of organic chemistry, for example by the reaction of a compound of the formula II with N-hydroxyphthalimide followed by treatment of the phthalimide so produced with hydrazine.

(c) For the production of those compounds of the formula I wherein $R^1$ and $R^2$ are linked, the cyclisation, conveniently in the presence of a suitable acid as defined hereinbefore, of a compound of the formula VI

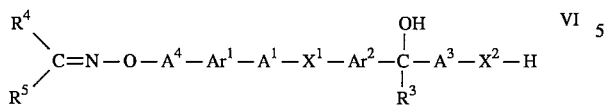

with an appropriate aldehyde or ketone, or with the corresponding hemiacetal or acetal derivative thereof.

The cyclisation reaction is conveniently performed in a suitable inert solvent or diluent, for example 1,2-dimethoxyethane or tetrahydrofuran. Preferably the reaction is performed using the approrpriate aldehyde or ketone as both a reactant and diluent. The cyclisation is effected at a temperature in the range, for example, 20° to 150° C., conveniently at or near the boiling point of the diluent or solvent.

The tertiary alcohol starting material of the formula VI may be obtained by standard procedures of organic chemistry.

The disclosures of European Patent Applications Nos. 0375457, 0385679 and 0409412, together with the procedures within processes (a) and (b) above for the preparation of appropriate oxime groups, are particularly relevant for the preparation of suitable starting materials.

Conventional protecting groups for an amino, imino, alkylamino or hydroxy group which may be present in $R^4$, $R^5$, $A^4$, $Ar^1$, $Ar^2$, $R^1$, $R^2$ or $R^3$ are set out hereinafter.

A suitable protecting group for an amino, imino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (*Prostaglandins, Leukotrienes Med.*, 1986, 22, 57; *Postaglandins*, 1984, 28, 666; *Brit. J. Pharmacol.*, 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–c):

Test a): $IC_{50}$ ($LTB_4$) in the range, for example, 0.01–40 µM $IC_{50}$ ($TxB_2$) in the range, for example 40–200 µM;

Test b): oral $ED_{50}(LTB_4)$ in the range, for example, 0.1–100 mg/kg;

Test c): oral $ED_{50}(LTB_4)$ in the range, for example, 0.1–50 mg/kg.

No overt toxicity or other untoward effects are present in tests b) and/or c) when compounds of the formula I are administered at several multiples of their minimum inhibitory dose or concentration.

Thus, by way of example, the compound acetone O-{4-[5-fluoro-3-(4-methoxytetrahydropyran-4-yl)phenylthio]benzyl}oxime has an $IC_{50}$ of 0.15 μM against $LTB_4$ in test a) and an oral $ED_{50}$ of approximately 1 mg/kg versus $LTB_4$ in test c); and the compound acetone O-{4-[5-fluoro-3-(4-methoxytetrahydropyran-4-yl)phenylthiol-]-α-methylbenzyl}oxime has an $IC_{50}$ of 0.09 μM against $LTB_4$ in test a) and an oral $ED_{50}$ of approximately 1.5 mg/kg versus $LTB_4$ in test c). In general those compounds of the formula I which are particularly preferred have an $IC_{50}$ of <1 μM against $LTB_4$ in test a) and an oral $ED_{50}$ of <100 mg/kg against $LTB_4$ in tests b) and/or c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an oxime derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an oxime derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an oxime derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an oxime derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the structures of the end-products of the formula I were confirmed by NMR and mass spectral techniques; unless otherwise stated, $CDCl_3$ solutions of the end-products of the formula I were used for the determination of the NMR spectral data, chemical shift values were measured on the delta scale and the following abbreviations are used: s, singlet; d, doublet; t, triplet; q, quartet; m, multipier;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(viii) the following abbreviations have been used:

| THF | tetrahydrofuran; |
|---|---|
| DMF | N,N-dimethylformamide; |
| NMP | N-methylpyrrolidin-2-one. |

EXAMPLE 1

Sodium hydride (60% w/w dispersion in mineral oil, 0.02 g) was added to a stirred mixture of acetone oxime (0.036 g), 4-[3-(4-chloromethylphenylthio)-5-fluorophenyl]-4-methoxytetrahydropyran (0.08 g) and DMF (2 ml) and the mixture was stirred at ambient temperature for 2 hours. Acetic acid (0.2 ml) and water (20 ml) were added and the mixture was extracted with diethyl ether. The organic phase was washed with brine, dried ($Na_2SO_4$) and evaporated. The residue was purified by column chromatography using increasingly polar mixtures of hexane and ethyl acetate as eluent. There was thus obtained acetone O-{4-[5-fluoro-3-(4-methoxytetrahydropyran-4-yl)phenylthio]benzyl}oxime as an oil (0.06 g, 68%).

NMR Spectrum: 1.88–1.95 (m, 10H), 2.97 (s, 3H), 3.80 (m, 4H), 5.07 (s, 2H), 6.80 (m, 1H), 6.90 (m, 1H), 7.10 (m, 1H), 7.37 (m, 4H).

The 4-[3-(4-chloromethylphenylthio)-5-fluorophenyl]-4-methoxytetrahydropyran used as a starting material was obtained as follows:

A mixture of 4-(5-fluoro-3-mercaptophenyl)-4-methoxytetrahydropyran (European Patent Application No. 0420511, Example 4 thereof; 2.42 g), potassium hydroxide (0.56 g) and DMF (25 ml) was stirred and heated to 140° C. until a clear solution was obtained. 4-Bromobenzaldehyde (2.78 g) and cuprous oxide (0.715 g) were added and the mixture was stirred and heated to 140° C. for 90 minutes. The mixture was cooled to ambient temperature and partitioned between diethyl ether and water. The organic phase was washed with brine, dried ($MgSO_4$) and evaporated. The residue was purified by column chromatography using a 4:1 mixture of petroleum ether (b.p. 40°–60° C.) and ethyl acetate as eluent. There was thus obtained 4-[5-fluoro-3-(4-methoxytetrahydropyran-4-yl)phenylthio]benzaldehyde (2.38 g, 68%), m.p. 93° C.

Sodium borohydride (0.1 g) was added to a stirred mixture of a portion (0.87 g) of the benzaldehyde so obtained and ethanol (20 ml). The mixture was stirred at ambient temperature for 30 minutes. Acetic acid (1 ml) and water (50 ml) were added and mixture was extracted with diethyl ether. The organic phase was washed with brine, dried ($Na_2SO_4$) and evaporated. The residue was purified by column chromatography using increasingly polar mixtures of hexane and ethyl acetate as eluent. There was thus obtained 4-[5-fluoro-3-(4-hydroxymethyphenylthio)phenyl]-4-methoxytetrahydropyran as a gum (0.85 g, 97%).

NMR Spectrum: 1.91 (m, 4H), 2.98 (s, 3H), 3.80 (m, 4H), 4.72 (s, 2H), 6.79 (m, 1H), 6.92 (m, 1H), 7.10 (m, 1H), 7.39 (m, 4H).

Thionyl chloride (0.1 ml) was added to a stirred mixture of a portion (0,075 g) of the material so obtained and methylene chloride (5 ml) and the mixture was stirred at ambient temperature for 30 minutes. The mixture was evaporated, toluene (5 ml) was added and the mixture was evaporated. There was thus obtained 4-[3-(4-chloromethylphenylthio)-5-fluorophenyl]-4-methoxytetrahydropyran as a gum (0.08 g) which was used without further purification.

EXAMPLE 2

Using an analogous procedure to that described in Example 1 except that the reactants were heated to 60° C. for 2 hours, acetone oxime was reacted with 4-{3-[4-(1-chloroethyl)phenylthio]-5-fluorophenyl}-4-methoxytetrahydropyran to give acetone O-{4-[5-fluoro-3-(4-methoxytetrahydropyran-4-yl)phenylthio]-α-methylbenzyl}oxime as an oil in 58% yield.

NMR Spectrum: 1.51 (d, 3H), 1.84 (s, 3H), 1.89 (m, 4H), 1.92 (s, 3H), 2.97 (s, 3H), 3.81 (m, 4H), 5.18 (q, 1H), 6.8 (m, 1H), 6.9 (m, 1H), 7.09 (m, 1H), 7.46 (m, 4H).

The 4-{3-[4-(1-chloroethyl)phenylthio]-5-fluorophenyl}-4-methoxytetrahydropyran used as a starting material was obtained as follows:

Methylmagnesium bromide (3M in THF; 2 ml) was added dropwise to a stirred solution of 4-[5-fluoro-3-(4-methoxytetrahydropyran-4-yl)phenylthio]benzaldehyde (1.73 g) in THF (20 ml). The mixture was stirred at ambient temperature for 30 minutes. Acetic acid (1 ml) and water (30 ml) were added and the mixture was extracted with diethyl ether. The organic phase was washed with brine, dried ($Na_2SO_4$) and evaporated.

The residue was purified by column chromatograph using increasingly polar mixtures of hexane and ethyl acetate as eluent. There was thus obtained 4-{5-fluoro-3-[4-(1-hydroxyethyl)phenylthio]phenyl}-4-methoxytetrahydropyran as an oil (1.7 g, 94%).

NMR Spectrum: 1.51 (d, 3H), 1.92 (m, 4H), 2.97 (s, 3H), 3.80 (m, 4H), 4.92 (q, 1H), 6.79 (m, 1H), 6.91 (m, 1H), 7.10 (m, 1H), 7.39 (m, 4H).

A mixture of a portion (0.36 g) of the material so obtained, pyridine (0.2 g) and methylene chloride (5 ml) was added dropwise to a stirred solution of thionyl chloride (0.2 ml) in methylene chloride (5 ml) which had been cooled to 0° C. The mixture was stirred at ambient temperature for 1 hour. The mixture was evaporated and the residue was partitioned between diethyl ether and water. The organic phase was dried (Na$_2$SO$_4$) and evaporated. There was thus obtained 4-{3-[4-(1-chloroethyl)phenylthio]-5-fluorophenyl}-4-methoxytetrahydropyran as an oil (0.38 g, 100%).

NMR Spectrum 1.85 (d, 3H), 1.90 (m, 4H), 2.98 (s, 3H), 3.80 (m, 4H), 5.08 (q, 1H), 6.87 (m, 1H), 6.96 (m, 1H), 7.14 (m, 1H), 7.38 (m, 4H).

EXAMPLE 3

Using an analogous procedure to that described in Example 1, benzophenone oxime was reacted with 4-[3-(4-chloromethylphenylthio)-5-fluorophenyl]-4-methoxytetrahydropyran to give benzophenone O-{4-[5-fluoro-3-(4-methoxytetrahydropyran-4-yl)phenylthio]benzyl}oxime as an oil in 44% yield.

NMR Spectrum: 1.9 (m, 4H), 2.95 (s, 3H), 3.8 (m, 4H), 5.24 (s, 2H), 6.82 (m, 1H), 6.92 (m, 1H), 7.1 (m, 1H), 7.3–7.5 (m, 14H).

EXAMPLE 4

Using an analogous procedure to that described in Example 1 except that the reactants were heated to 60° C. for 2 hours, benzophenone oxime was reacted with 4-{3-[4-(1-chloroethyl)phenylthio]-5-fluorophenyl}-4-methoxytetrahydropyran to give benzophenone O-{4-[5-fluoro-3-(4-methoxytetrahydropyran-4-yl)phenylthio]-α-methylbenzyl}-oxime as an oil in 38% yield.

NMR Spectrum: 1.55 (d, 3H), 1.9 (m, 4H), 2.95 (s, 3H), 3.78 (m, 4H), 5.4 (q, 1H), 6.8 (m, 1H), 6.9 (m, 1H), 7.09 (m, 1H), 7.3–7.5 (m, 14H).

EXAMPLE 5

Using an analogous procedure to that described in Example 1, tetrahydropyran-4-one oxime was reacted with 4-{3-[4-(1-chloroethyl)-phenylthio] -5-fluorophenyl}-4-methoxytetrahydropyran to give tetrahydropyran-4-one O-{4-[5-fluoro-3-(4-methoxytetrahydropyran-4-yl)-phenylthio]-α-methylbenzyl}oxime as an oil in 74% yield.

NMR Spectrum: 1.52 (d, 3H), 1.89 (m, 4H), 2.33 (m, 2H), 2.69 (m, 2H), 2.97 (s, 3H), 3.77 (m, 8H), 5.20 (q, 1H), 6.79 (m, 1H), 6.91 (m, 1H), 7.11 (m, 1H), 7.34 (m, 4H).

The tetrahydropyran-4-one oxime used as a starting material was obtained as follows:

A mixture of tetrahydropyran-4-one (1 g), hydroxylamine hydrochloride (1 g), sodium acetate (2 g) and ethanol (10 ml) was stirred and heated to reflux for 1 hour. The mixture was evaporated and the residue was partitioned between diethyl ether and water. The organic phase was dried (Na$_2$SO$_4$) and evaporated. The residue was recrystallised from a mixture of hexane and ethyl acetate. There was thus obtained tetrahydropyran-4-one oxime (0.75 g, 65%), m.p. 86°–87° C.

EXAMPLE 6

A mixture of pyridine-2-carboxaldehyde (0.05 g), O-{4-[5-fluoro-3-(4-methoxytetrahydropyran-4-yl)phenylthio]benzyl}hydroxylamine (0.09 g), glacial acetic acid (0.02 g) and ethanol (2 ml) was stirred and heated to reflux for 1 hour. The mixture was cooled to ambient temperature and partitioned between ethyl acetate and water. The organic phase was washed with water, dried (Na$_2$SO$_4$) and evaporated. The residue was purified by column chromatography using increasingly polar mixtures of hexane and ethyl acetate as eluent. There was thus obtained (E)-pyridine-2-carboxaldehyde . O-{4-[5-fluoro-3-(4-methoxytetrahydropyran-4-yl)phenylthio]benzyl}oxime as a gum (0.08 g, 75%).

NMR Spectrum: 1.75–2.05 (m, 4H), 2.96 (s, 3H), 3.75–3.90 (m, 4H), 5.26 (s, 2H), 6.83 (m, 1H), 6.92 (m, 1H), 7.12 (m, 1H), 7.25 (m, 1H), 7.40 (s, 4H), 7.6–7.85 (m, 2H), 8.24 (s, 1H), 8.62 (m, 1H).

The O-{4-[5-fluoro-3-(4-methoxytetrahydropyran-4-yl)phenylthio]benzyl}hydroxylamine used as a starting material was obtained as follows:

A mixture of 4-[3-(4-chloromethylphenylthio)-5-fluorophenyl]-4-methoxytetrahydropyran (0.73 g), N-hydroxyphthalimide (0.41 g), potassium carbonate (0.31 g) and DMF (2 ml) was stirred at ambient temperature for 18 hours. The mixture was acidified to pH5 by the addition of glacial acetic acid and partitioned between diethyl ether and water. The organic phase was washed with water and with brine, dried (Na$_2$SO$_4$) and evaporated. The residue was purified by column chromatography using increasingly polar mixtures of hexane and ethyl acetate as eluent. There was thus obtained N-{4-[5-fluoro-3-(4-methoxytetrahydropyran-4-yl)phenylthio]benzyloxy}phthalimide as a gum (0.4 g, 41%).

A mixture of a portion (0.35 g) of the phthalimide so obtained, hydrazine hydrate (0.2 ml) and methanol (10 ml) was stirred and heated to reflux for 1 hour. The mixture was cooled to ambient temperature, filtered and evaporated. The residue was purified by column chromatography using increasingly polar mixtures of hexane and ethyl acetate as eluent. There was thus obtained the required starting material as a gum (0.23 g, 89%).

EXAMPLE 7

Using an analogous procedure to that described in Example 6, 5-nitrofuran-2-carboxaldehyde was reacted with O-{4-[5-fluoro-3-(4-methoxytetrahydropyran-4-yl)phenylthio]benzyl}hydroxylamine to give 5-nitrofuran-2-carboxaldehyde O-{4-[5-fluoro-3-(4-methoxytetrahydropyran-4-yl)phenylthio]benzyl}oxime as a gum in 58% yield.

NMR Spectrum 1.8–2.05 (m, 4H), 2.97 (s, 3H), 3.75–3.95 (m, 4H), 5.25 and 5.32 (2 s's, 2H), 6.33 and 7.33 (2 d's, 1H), 6.8–7.0 (m, 2H), 7.13 (m, 1H), 7.3–7.5 (m, 5H), 7.53 and 8.04 (2 s's, 1H).

EXAMPLE 8

Using an analogous procedure to that described in Example 1, acetone oxime was reacted with 4-[3-(4-chloromethylbenzyloxy)-5-fluorophenyl]-4-methoxytetrahydropyran to give acetone O-{4-[5-fluoro-3-(4-methoxytetrahydropyran-4-yl)phenoxymethyl]benzyl}oxime as a gum in 72% yield.

NMR Spectrum 1.8–2.05 (m, 10H), 2.97 (s, 3H), 3.55–3.70 (m, 4H), 5.04 (s, 2H), 5.07 (s, 2H), 6.61 (m, 1H), 6.70 (m, 1H), 6.80 (m, 1H), 7.39 (t, 4H).

The 4-[3-(4-chloromethylbenzyloxy)-5-fluorophenyl]-4-methoxytetrahydropyran used as a starting material was obtained as follows:

A mixture of 1,4-benzenedimethanol (4.14 g), sodium hydride (60% w/w dispersion in mineral oil, 0.6 g) and NMP (25 ml) was stirred at ambient temperature for 1 hour. 4-(3,5-Difluorophenyl)-4-methoxytetrahydropyran (European Patent Application No. 0462813, Example 5 thereof; 3.42 g) was added and the mixture was stirred at ambient temperature for 18 hours and then heated to 60° C. for 6 hours. The mixture was cooled to ambient temperature and acidified by the addition of glacial acetic acid (5 ml). The mixture was partitioned between diethyl ether and water. The organic phase was washed with water, dried ($Na_2SO_4$) and evaporated to dryness. The residue was purified by column chromatography using increasingly polar mixtures of hexane and ethyl acetate as eluent. There was thus obtained 4-[5-fluoro-3-(4-hydroxymethylbenzyloxy)phenyl]-4-methoxytetrahydropyran as a solid in 67% yield.

The alcohol so obtained was chlorinated using an analogous procedure to that described in the last paragraph of the portion of Example 1 which is concerned with the preparation of starting materials. There was thus obtained 4-[3-(4-chloromethylbenzyloxy)-5-fluorophenyl]-4-methoxytetrahydropyran as a gum which was used without further purification.

EXAMPLE 9

Using an analogous procedure to that described in Example 1, acetone oxime was reacted with 4-[3-(3-chloro-4-chloromethylphenylthio)-5-fluorophenyl]-4-methoxytetrahydropyran to give acetone O-{2-chloro-4-[5-fluoro-3-(4-methoxytetrahydropyran-4-yl)phenylthio]benzyl}oxime as a gum in 50% yield.

NMR Spectrum 1.8–2.05 (m, 10H), 2.98 (s, 3H), 3.75–3.90 (m, 4H), 5.15 (s, 2H), 6.88 (m, 1H), 6.97 (m, 1H), 7.15 (m, 1H), 7.25 (m, 1H), 7.37 (m, 2H).

The 4-[3-(3-chloro-4-chloromethylphenylthio)-5-fluorophenyl]-4-methoxytetrahydropyran used as a starting material was obtained as follows:

A mixture of 2-chloro-4-fluorobenzaldehyde (0.526 g) 4-(5-fluoro-3-mercaptophenyl)-4-methoxytetrahydropyran (0.726 g), potassium carbonate (0.46 g) and DMF (5 ml) was stirred and heated to 120° C. for 30 minutes. The mixture was cooled to ambient temperature and partitioned between diethyl ether and water. The organic phase was washed with brine, dried ($Na_2SO_4$) and evaporated. The residue was purified by column chromatography using increasingly polar mixtures of hexane and ethyl acetate as eluent. There was thus obtained 2-chloro-4-[5-fluoro-3-(4-methoxytetrahydropyran-4-yl)phenylthio]benzaldehyde as a gum (1.1 g, 96%).

NMR Spectrum 1.8–2.0 (m, 4H), 3.01 (s, 3H), 3.8–3.9 (m, 4H), 7.1–7.2 (m, 4H), 7.33 (m, 1H), 7.81 (d, 1H), 10.37 (s, 1H).

Using analogous procedures to those described in the second and third paragraphs of the portion of Example 1 which is concerned with the preparation of starting materials, the benzaldehyde so obtained was converted into 4-[3-(3-chloro-4-chloromethylphenylthio)-5-fluorophenyl]-4-methoxytetrahydropyran.

EXAMPLE 10

The following illustrate representative pharmaceutical dosage forms containing the compound of formula I, or a pharmaceutically-acceptable salt thereof (hereafter compound X), for therapeutic or prophylactic use in humans:

| | (a) Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | |
| | Compound X | 2.5 |

| | |
|---|---|
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

We claim:

1. An oxime derivative of the formula I

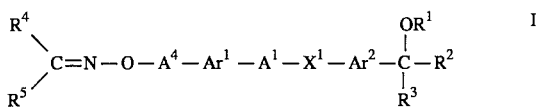

wherein $R^4$ and $R^5$ together form a group of the formula $-A^2-O-A^3-$ which together with the carbon atom to which $A^2$ and $A^3$ are attached define a ring having 5 or 6 ring atoms, wherein each of $A^2$ and $A^3$ is independently (1–3C)alkylene, and which ring may optionally bear one or two substituents selected from hydroxy, (1–4C)alkyl and (1–4C)alkoxy;

$A^4$ is (1–4C)alkylene which may optionally bear one or two substituents selected from (1–4C)alkyl, phenyl and phenyl-(1–4C)alkyl;

wherein each phenyl or phenyl-(1–4C)alkyl group may optionally bear one or two substituents selected from halogeno, cyano, trifluoromethyl, hydroxy, amino, nitro, (1–4C)alkyl, (1–4C)alkoxy, (1–4C)alkylamino, di-(1–4C)alkylamino, (1–4C)alkylthio, (1–4C)alkylsulphinyl and (1–4C)alkylsulphonyl;

$Ar^1$ is phenylene, pyridinediyl or pyrimidinediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$A^1$ is a direct link to $X^1$, or $A^1$ is (1–4C)alkylene;

$X^1$ is oxy, thio, sulphinyl or sulphonyl;

$Ar^2$ is phenylene, pyridinediyl, pyrimidinediyl, thiophenediyl, furandiyl or thiazolediyl which may optionally bear one or two substituents selected from halogeno, cyano, trifluoromethyl, hydroxy, amino, (1–4C)alkyl, (1–4C)alkoxy, (1–4C)alkylamino and di-(1–4C)alkylamino;

$R^1$ is hydrogen, (1–4C)alkyl, (3–4C)alkenyl or (3–4C)alkynyl; and $R^2$ and $R^3$ together form a group of the formula $-A^2-X^2-A^3-$ which together with the carbon atom to which $A^2$ and $A^3$ are attached define a ring having 5 or 6 ring atoms, wherein each of $A^2$ and $A^3$ is independently (1–3C)alkylene and $X^2$ is oxy, and which ring may optionally bear one or two substituents selected from hydroxy, (1–4C)alkyl and (1–4C)alkoxy;

or a pharmaceutically-acceptable salt thereof.

2. An oxime derivative of the formula I as claimed in claim 1 wherein $R^4$ and $R^5$ together form a group of the formula $-A^2-O-A^3-$ wherein $A^2$ is methylene or ethylene and $A^3$ is ethylene;

$A^4$ is methylene which may optionally bear one or two substituents selected from methyl, ethyl, phenyl and benzyl, and wherein said phenyl or benzyl group may optionally bear one or two substituents selected from fluoro, chloro, methyl and methoxy;

$Ar^1$ is 1,4-phenylene which may optionally bear one substituent selected from fluoro, chloro, methyl and methoxy, or $Ar^1$ is 2,5-pyridinediyl (with the $A^1$ group in the 2-position);

$A^1$ is a direct link to $X^1$ and $X^1$ is thio, or $A^1$ is methylene and $X^1$ is oxy;

$Ar^2$ is 1,3- or 1,4-phenylene which may optionally bear one or two substituents selected from fluoro, chloro, trifluoromethyl, amino, methyl and methoxy, or $Ar^2$ is 3,5-pyridinediyl, 4,6-pyrimidinediyl, 2,4-thiophenediyl, 2,5-thiophenediyl, 2,4-thiazolediyl or 2,5-thiazolediyl;

$R^1$ is hydrogen, methyl, ethyl or allyl; and $R^2$ and $R^3$ together form a group of the formula $-A^2-X^2-A^3-$ which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may optionally bear one or two substituents selected from methyl and ethyl;

or a pharmaceutically-acceptable salt thereof.

3. An oxime derivative of the formula I as claimed in claim 1 wherein $R^4$ and $R^5$ together form a group of the formula $-A^2-O-A^3-$ wherein each of $A^2$ and $A^3$ is ethylene;

$A^4$ is methylene which may optionally bear a methyl substituent;

$Ar^1$ is 1,4-phenylene or 2-chloro-1,4-phenylene (with the $A^1$ group in the 4-position);

$A^1$ is a direct link to $X^1$ and $X^1$ is thio, or $A^1$ is methylene and $X^1$ is oxy;

$Ar^2$ is 1,3-phenylene or 5-fluoro-1,3-phenylene;

$R^1$ is methyl; and $R^2$ and $R^3$ together form a group of the formula $-A^2-X^2-A^3-$ which together with the carbon atom to which $A^2$ and $A^3$ are attached define a ring having 6 ring atoms, wherein each of $A^2$ and $A^3$ is ethylene and $X^2$ is oxy, and which ring may optionally bear a methyl substituent alpha to $X^2$;

or a pharmaceutically-acceptable salt thereof.

4. An oxime derivative of the formula I, or a pharmaceutically-acceptable salt thereof, as claimed in claim 1, being tetrahydropyran-4-one O-{4-[5-fluoro-3-(4-methoxytetrahydropyran-4-yl)-phenylthio]-α-methylbenzyl}-oxime.

5. A pharmaceutical composition which comprises an oxime derivative of the formula I, or a pharmaceutically-acceptable salt thereof, as claimed in any one of claims 2, 3, and 4 in association with a pharmaceutically-acceptable diluent or carrier.

6. A method of treating a disease or medical condition mediated alone or in part by one or more leukotrienes which comprises administering to a warm-blooded animal requiring such treatment an effective amount of an oxime derivative of the formula I, or a pharmaceutically-acceptable salt thereof, as claimed in any one of claims 1, 3, 5 and 4.

* * * * *